(12) United States Patent
Lederman et al.

(10) Patent No.: US 11,173,278 B2
(45) Date of Patent: Nov. 16, 2021

(54) THREE-DIMENSIONAL RIGHT ATRIAL APPENDAGE CURVE CATHETER

(71) Applicants: The United States of America, as represented by the Secretary, Department of Health and Human Services, Bethesda, MD (US); Henry Ford Health System, Detroit, MI (US)

(72) Inventors: Robert J. Lederman, Chevy Chase, MD (US); Toby Rogers, Washington, DC (US); Nasser Rafiee, Andover, MD (US); Adam B. Greenbaum, Detroit, MI (US); William W. O'Neill, Grosse Point Farms, MI (US)

(73) Assignees: The USA, as represented by the Secretary, Dept. of Health and Human Services, Bethesda, MD (US); Henry Ford Health System, Detroit, MI (US)

( * ) Notice: Subject to any disclaimer, the term of this patent is extended or adjusted under 35 U.S.C. 154(b) by 534 days.

(21) Appl. No.: 15/571,342

(22) PCT Filed: May 9, 2016

(86) PCT No.: PCT/US2016/031461
§ 371 (c)(1),
(2) Date: Nov. 2, 2017

(87) PCT Pub. No.: WO2016/186880
PCT Pub. Date: Nov. 24, 2016

(65) Prior Publication Data
US 2018/0214667 A1 Aug. 2, 2018

Related U.S. Application Data

(60) Provisional application No. 62/162,453, filed on May 15, 2015.

(51) Int. Cl.
*A61M 25/00* (2006.01)
*A61B 18/14* (2006.01)
(Continued)

(52) U.S. Cl.
CPC ... *A61M 25/0041* (2013.01); *A61B 17/00234* (2013.01); *A61B 17/3415* (2013.01);
(Continued)

(58) Field of Classification Search
CPC .......... A61M 25/0041; A61M 25/0082; A61M 25/09041; A61M 25/10; A61B 17/00234;
(Continued)

(56) References Cited

U.S. PATENT DOCUMENTS 5,269,326 A 12/1993 Verrier
5,306,262 A 4/1994 Weldon
(Continued)

FOREIGN PATENT DOCUMENTS

| JP | 2008-531086 | 8/2008 |
| JP | 2014-087695 | 5/2014 |

(Continued)

OTHER PUBLICATIONS

Notification of the First Office Action for CN Application No. 201680027776.X, dated Dec. 25, 2019, 20 pages (with an English translation).
(Continued)

*Primary Examiner* — Tiffany Legette
(74) *Attorney, Agent, or Firm* — Sheridan Ross P.C.

(57) ABSTRACT

Disclosed delivery catheters have a three-dimensional curvature that facilitates reaching the RAA from the inferior vena cava, positioning the distal end of the catheter generally parallel to the plane of the pericardial space at the puncture location within the RAA, orienting the puncturing device in a direction that avoids the right coronary artery,
(Continued)

aorta, pulmonary artery, and other structures to prevent bystander injury to such structures, and provides sufficient rigidity to puncture through a wall of the RAA into the pericardial space.

8 Claims, 10 Drawing Sheets

(51) Int. Cl.
| | |
|---|---|
| *A61B 17/00* | (2006.01) |
| *A61B 17/34* | (2006.01) |
| *A61B 17/22* | (2006.01) |
| *A61B 17/12* | (2006.01) |
| *A61M 25/09* | (2006.01) |
| *A61M 25/10* | (2013.01) |

(52) U.S. Cl.
CPC .... *A61B 18/1492* (2013.01); *A61B 17/12122* (2013.01); *A61B 2017/003* (2013.01); *A61B 2017/00243* (2013.01); *A61B 2017/00331* (2013.01); *A61B 2017/22069* (2013.01); *A61M 25/0082* (2013.01); *A61M 25/09041* (2013.01); *A61M 25/10* (2013.01)

(58) Field of Classification Search
CPC .......... A61B 17/3415; A61B 17/12122; A61B 18/1492; A61B 201/00243; A61B 201/003; A61B 201/00331; A61B 201/22069
See application file for complete search history.

(56) References Cited

U.S. PATENT DOCUMENTS

| | | | |
|---|---|---|---|
| 5,814,028 A | 9/1998 | Swartz et al. | |
| 5,902,289 A | 5/1999 | Swartz et al. | |
| 5,968,010 A | 10/1999 | Waxman et al. | |
| 6,132,417 A * | 10/2000 | Kiesz | A61M 25/0041 604/264 |
| 6,200,303 B1 | 3/2001 | Verrior et al. | |
| 7,226,440 B2 | 6/2007 | Gelfand et al. | |
| 8,852,173 B2 | 10/2014 | Sigg et al. | |
| 8,882,765 B2 | 11/2014 | Kassab et al. | |
| 8,894,606 B2 | 11/2014 | Kassab et al. | |
| 2004/0030266 A1 * | 2/2004 | Murayama | B21F 15/08 600/585 |
| 2005/0234436 A1 | 10/2005 | Baxter et al. | |
| 2005/0234437 A1 | 10/2005 | Baxter et al. | |

FOREIGN PATENT DOCUMENTS

| | | |
|---|---|---|
| WO | WO 2006/091597 | 8/2006 |
| WO | WO 2008/112870 | 9/2008 |
| WO | WO 2013/013098 | 1/2013 |
| WO | WO 2014/066383 | 5/2014 |

OTHER PUBLICATIONS

Mickelsen et al., "Transvenous Access to the Pericardial Space: An Approach to Epicardial Lead Implantation for Cardiac Resynchronization Therapy," *Pacing and Clinical Electrophysiology*, 28(10):1018-1024 (Oct. 2005).
Supplemental Search Report for related European Application No. EP 16796939.3, dated Dec. 21, 2018, 9 pages.
International Search Report and Written Opinion for related International Application No. PCT/US2016/031461, dated Aug. 16, 2016, 12 pages.
Official Action with English Translation for China Patent Application No. 201680027776.X, dated Jun. 10, 2020 13 pages.
Official Action with English Translation for China Patent Application No. 201680027776.X, dated Dec. 9, 2020 18 pages.
Official Action with English Translation for Japan Patent Application No. 2017-559396, dated Dec. 25, 2020 8 pages.

* cited by examiner

FIG. 10

THREE-DIMENSIONAL RIGHT ATRIAL APPENDAGE CURVE CATHETER

CROSS-REFERENCE TO RELATED APPLICATIONS

This application is the U.S. National Stage of International Application No. PCT/US2016/031461, filed May 9, 2016, which claims the benefit of U.S. Provisional Patent Application No. 62/162,453, filed May 15, 2015, which is entirely incorporated by reference herein.

FIELD

The present disclosure relates to catheters and other devices for accessing the pericardial space through the right atrium and right atrial appendage.

BACKGROUND

Some procedures require access to the pericardial space, such as for left atrial appendage ligation, circumferential tricuspid annuloplasty, or epicardial ablation for rhythm disorders. One way to access the pericardial space is by advancing a transvascular catheter through the right atrium and into the right atrial appendage, and passing the catheter through a puncture in the right atrial appendage into the pericardial space. However, such procedures can risk myocardial or coronary laceration, along with other risks.

SUMMARY

Described herein are curved catheters that are shaped and configured to more safely guide traversal of the right atrial appendage (RAA) and more effectively exit through the superior left sulcus wall of the RAA into the pericardial space in a desired orientation that reduces the risks of injuring bystander tissues and increases the success rate of procedures requiring access to the pericardial space.

Disclosed catheters can comprise a proximal segment, a transition segment extending distally from the proximal segment, a distal segment extending distally from the transition segment, and a distal end, wherein the transition segment and/or the distal segment are adapted to extend from the proximal segment with a clockwise spiral curvature when the catheter is positioned within a patient. When inserted into a patient, the proximal segment is positioned within the inferior vena cava, the transition segment extends across the caval-atrial junction and curves rightward, forward, and upward such that the catheter abuts a right lateral wall of the right atrium, and the distal segment curves leftward, forward, and upward from the transition segment through the right atrium such that the catheter abuts an anterior wall of the right atrium adjacent to the RAA, and the distal segment continues to curve leftward, rearward, and upward from the anterior wall of the right atrium along an anterior-superior wall of the RAA such that distal end of the catheter contacts a cephalad wall of the RAA. The catheter is configured to guide a coaxial puncturing device to extend from the distal end of the catheter and puncture through the superior left sulcal wall of the RAA into the pericardial space safely cephalad and away from critical structures such as coronary artery. The curvature of the catheter orients the distal end of the catheter pointing generally leftward and parallel with the pericardium such that the puncturing device passes through the cephalad wall of the RAA and into the pericardial space without damaging the pericardium and at a location spaced apart from the right coronary artery, the pulmonary artery, and the aorta to minimize the risk of damage such bystander structures. The catheter can be configured to deliver and/or be used with an inflatable balloon catheter that is inflated within the RAA to separate or flatten trabeculations within the RAA to facilitate advancing the distal end of the catheter against the left sulcal wall of the RAA.

The foregoing and other features and advantages of the disclosed technology will become more apparent from the following detailed description of several embodiments, which proceeds with reference to the accompanying figures.

BRIEF DESCRIPTION OF THE DRAWINGS

FIGS. 8A-8D are radiographic images illustrating an exemplary procedure using a curved catheter to engage the right atrial appendage from the inferior vena cava (FIG. 8A) and then aligning with and engaging against the outer or anterior wall of the right atrial appendage with the tip purchased against the cephalad left sulcus wall of the right atrial appendage (FIG. 8B). In FIG. 8C, a guidewire exits the curved catheter to traverse the wall of the right atrial appendage and enter the pericardial space, and in FIG. 8D a microcatheter is delivered through the curved catheter over the guidewire from the right atrium into the pericardial space.

DETAILED DESCRIPTION

The catheters, systems, and methods described herein can be used for performing various intrapericardial procedures, such as left atrial appendage suture ligation, epicardial ablation for rhythm disorders, and tricuspid annuloplasty. More information regarding such procedures as well as related systems and devices can be found in International Publication Number WO 2014/015842 A1, published Oct. 2, 2014, and entitled "DEVICES AND METHODS FOR TREATING FUNCTIONAL TRICUSPID VALVE REGURGITATION"; International Publication Number WO 2014/200764 A1, published Dec. 18, 2014, and entitled "ENCIRCLING IMPLANT DELIVERY SYSTEMS AND METHODS"; and International Publication Number WO 2015/061775 A1, published Apr. 30, 2015, and entitled "ATRIAL APPENDAGE LIGATION"; all of which are incorporated by reference herein in their entireties.

As used herein, the direction "right" refers to the right lateral side of a patient and the term "left" refers to the left lateral side of a patient. Similarly, the terms front and rear refer to the anterior and posterior sides of a patient. Terms such as "up" and "top" refer to the superior direction of a patient, and terms such as "down" and "bottom" refer to the inferior direction of a patient. The terms "distal" and "proximal" as used herein refer to proximal and distal ends of a catheter or other transvascular device, with the proximal direction being toward the point of insertion into the patient and the distal direction being toward the free end of the device.

Figure 1:
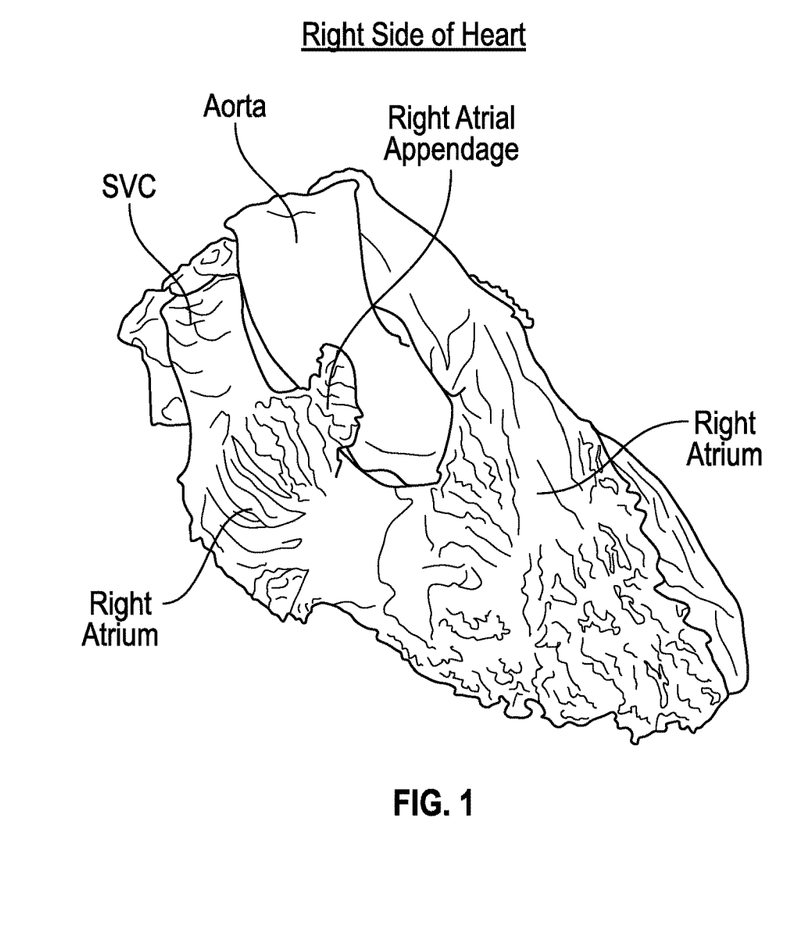
FIG. 1 shows a model representing the interior volume of a heart, as viewed from the right side. The right atrial appendage is in the foreground.
Figure 2:
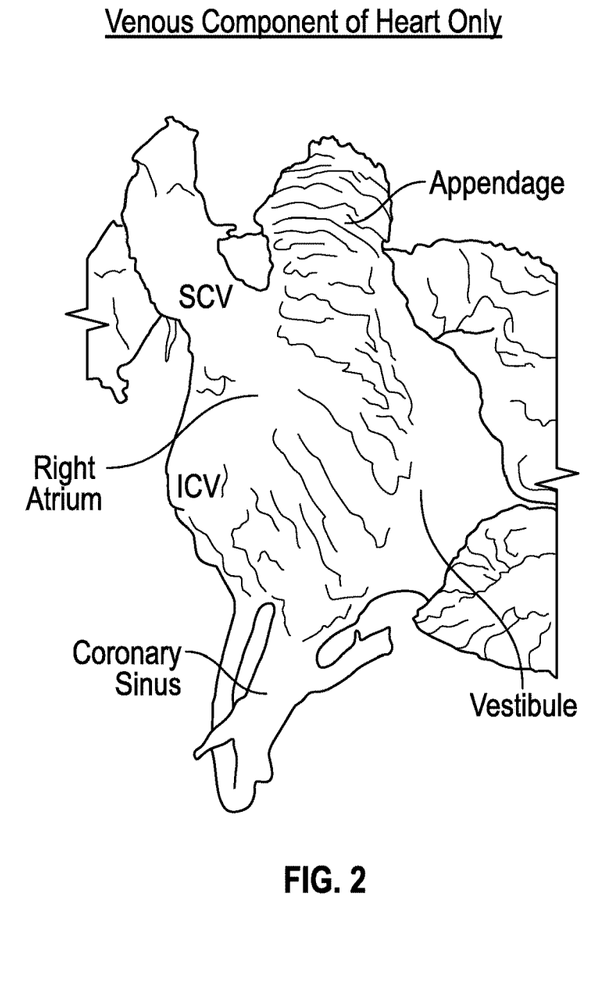
FIG. 2 shows a model representing the interior volume of only the venous structures of the heart.

FIGS. 1 and 2 show models of the interior volume of the heart, and in particular illustrate the geometry and orientation of the right atrium (RA) and the right atrial appendage (RAA). In FIG. 1, the entire interior of the heart is shown from the right side, while FIG. 2 shows only the de-oxygenated blood regions of the heart (e.g., the right side of the heart, vena cavas, pulmonary artery, etc.). As shown, the RA and RAA include irregular interior wall surfaces that form many small folds, flaps and crevices that can obstruct the delivery of the catheter device.

Disclosed delivery catheters have a three-dimensional curvature that facilitates reaching the RAA from the femoral vein via the inferior vena cava, positioning the distal end of the catheter generally parallel to the plane of the pericardial space at the puncture location within the RAA, orienting the puncturing device in a direction that avoids the right coronary artery, aorta, pulmonary artery, and left atrial appendage to prevent bystander injury to such structures, and provides sufficient rigidity to puncture through the cephalad wall of the RAA into the pericardial space.

Figure 3:
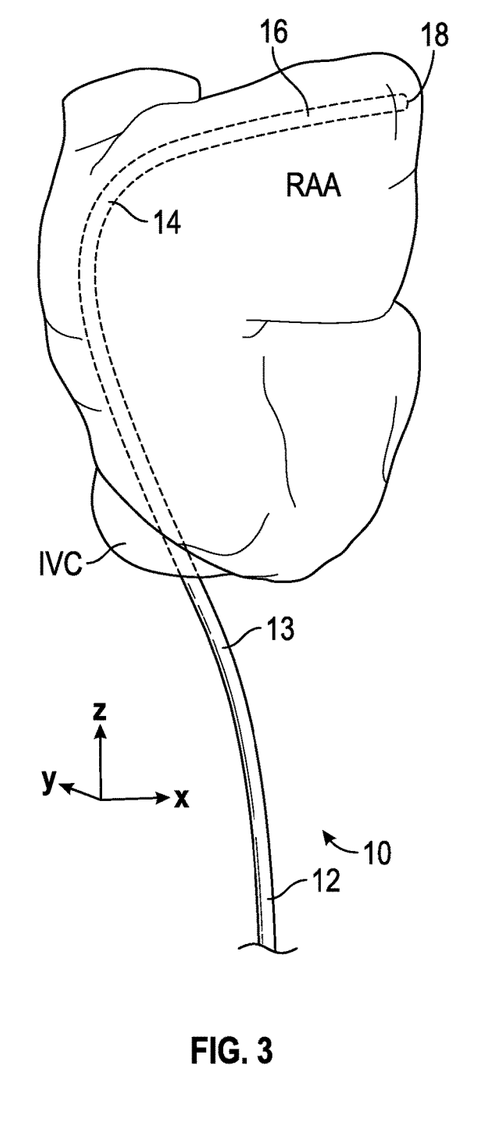
FIG. 3 illustrates an exemplary curved catheter extending through the inferior vena cava, through the right atrium, and into to the right atrial appendage abutting the cephalad left sulcal wall.
Figure 4:
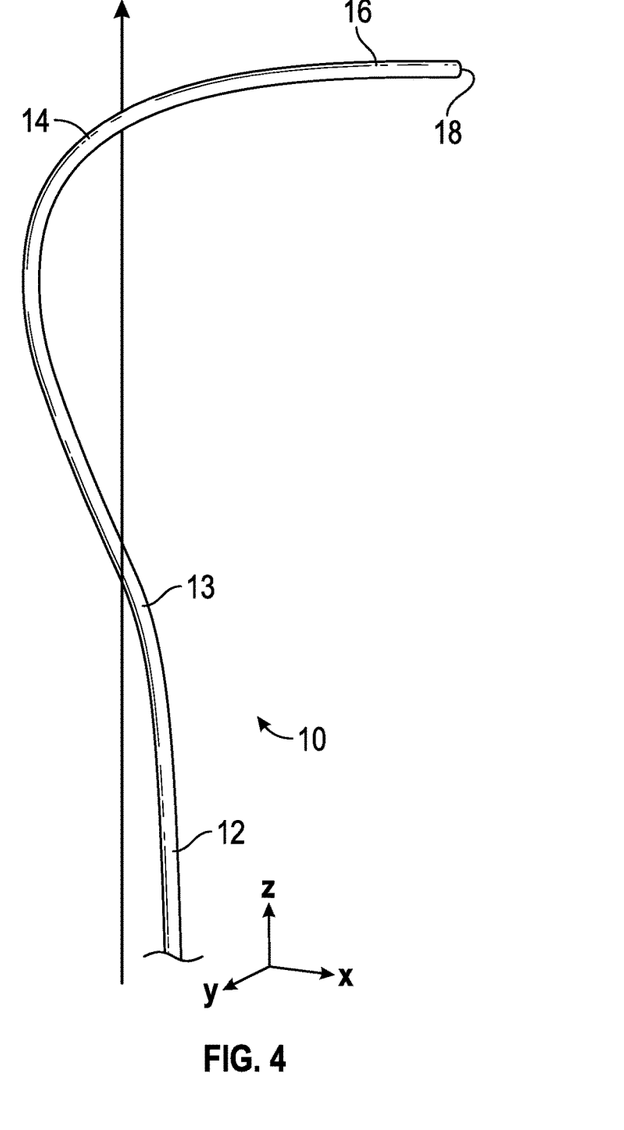
FIG. 4 illustrates the curved catheter of FIG. 3 in isolation.

FIG. 3 illustrates an exemplary curved catheter 10 extending through the IVC, through the RA, and into the RAA. The disclosed catheters include three segments, as illustrated in FIG. 4. A first, proximal segment 12 is generally straight or slightly curved and can project generally vertically through the IVC. A second, transitional segment 13 can be positioned in the vicinity of the caval-atrial junction to curve toward the right and front sides of the patient. As shown in FIG. 4, the catheter 10 passes behind a vertical z-axis at the transitional segment 13 and then curves around and passes in front of the z-axis at a third, distal segment 14, which curves more sharply toward the left side of the patient to the distal end 18 of the catheter when the catheter is positioned for use. The distal segment 10 can also include a substantially straight portion 16 at the distal end, which can extend generally transversely within the patient.

The transition segment 13 and distal segment 14 spiral clockwise from the proximal segment 12 toward to the straight distal portion 16. The spiral or helical curvature is illustrated in FIG. 4 with reference to a straight vertical z-axis. The terms "spiral" and "helix" are used interchangeably herein and are defined broadly herein to mean any three-dimensional curvature that curves around a central axis as the curvature also extends in the direction of the central axis, and such terms do not require the curvature to have a constant radius from the central axis (as in a circular helix), a constant pitch or tangent angle relative to the central axis (as in some helixes), a continuously increasing or decreasing radius from the central axis (as in some spirals), a straight central axis, or any minimum arc length around the central axis, though all such species are included within the definition. The term "clockwise" means that the catheter curves with a right-handed chirality such that a catheter with a clockwise curvature appears to curve in a generally clockwise path when viewing the catheter from the proximal segment looking upward/distally along the vertical z-axis.

Figure 5A:
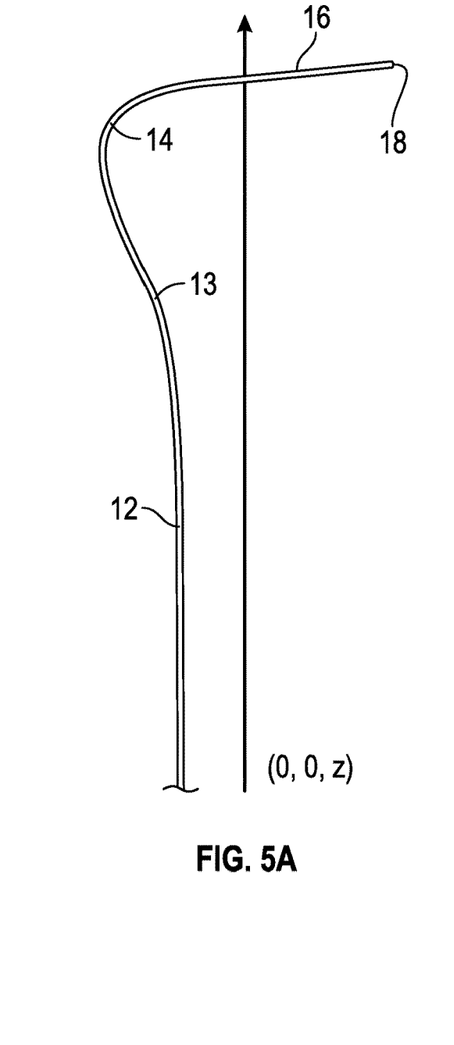
FIGS. 5A-5H show various side views of the curved catheter of FIG. 4 as the catheter is rotated about a vertical axis.
Figures 5B, 5C:
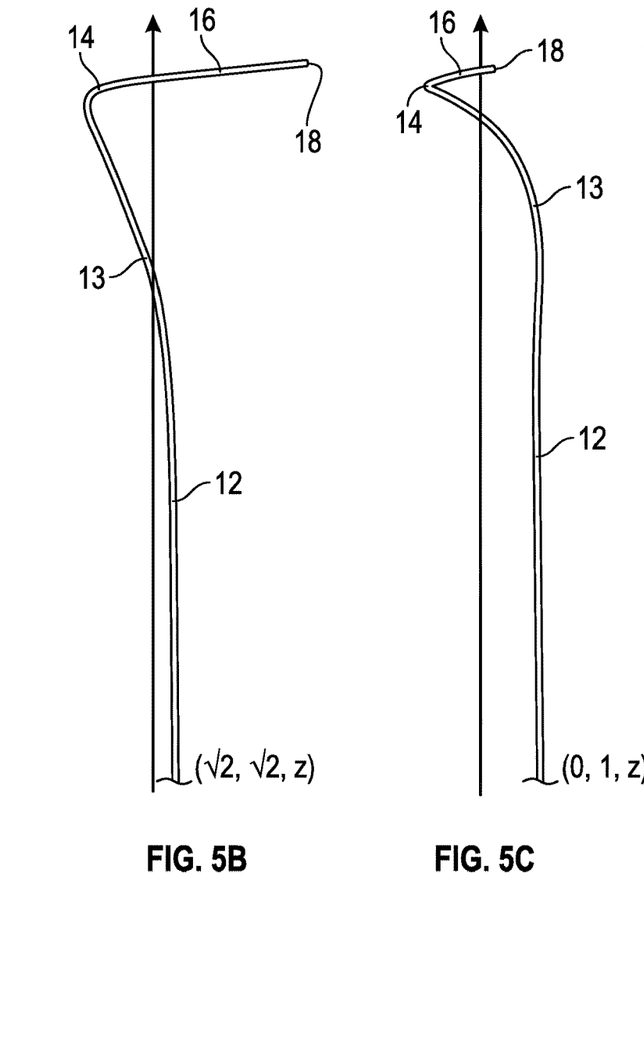
Figure 5D:
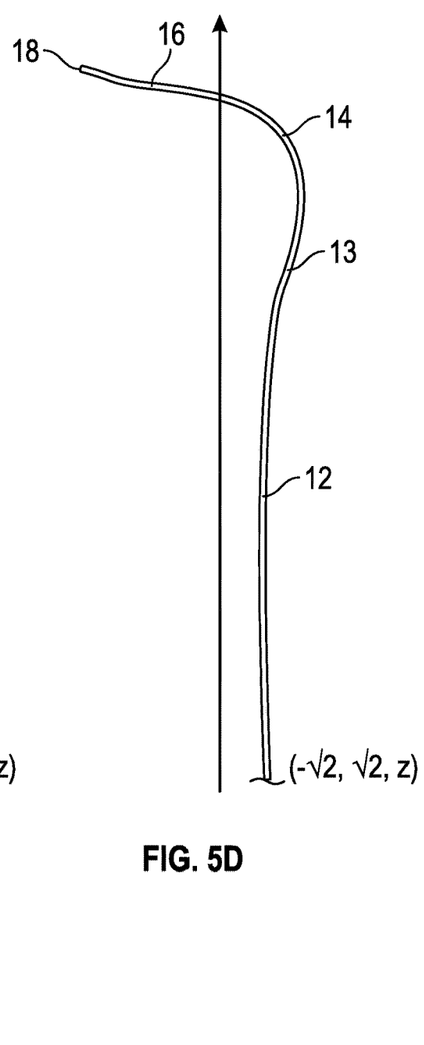
Figure 5E:
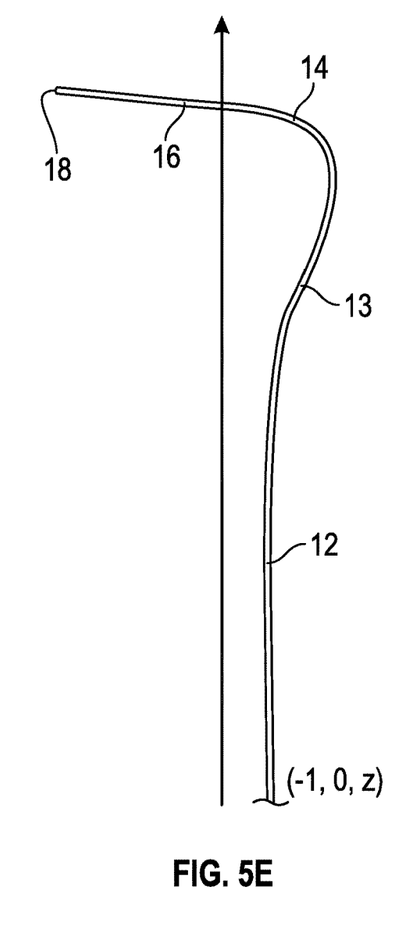
Figure 5F:
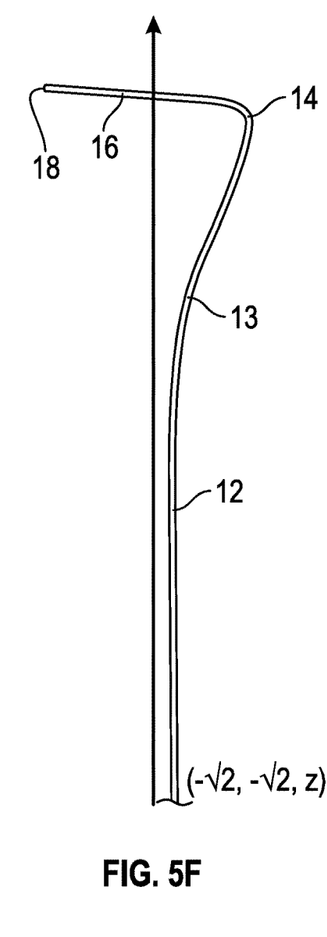
Figure 5G:
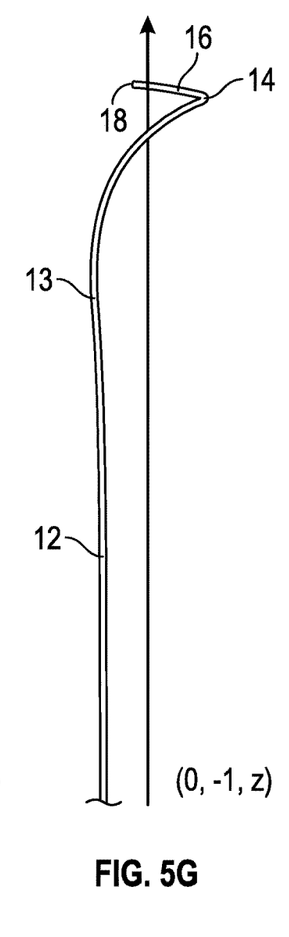
Figure 5H:
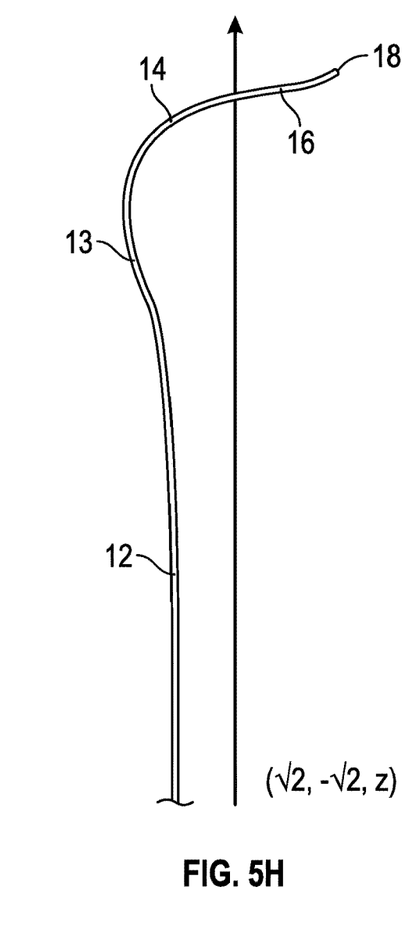

The curvature of the catheter 10 is further illustrated in FIGS. 5A-5H, which show eight side elevation views taken at 45° increments around the z-axis. FIG. 5A is front view, FIG. 5B is a front-left view (similar to the views of FIGS. 3 and 4), FIG. 5C is a left side view, FIG. 5D is a rear-left view, FIG. 5E is a rear view, FIG. 5F is a rear-right view, FIG. 5G is a right side view, and FIG. 5H is a front-left view. As shown in FIGS. 5A-5H, the catheter 10 curves rightward and forward at the transitional segment 13. The catheter 10 then curves leftward and rearward at the distal segment 14, such that the distal end 18 projects leftward and slightly upward and rearward. This trajectory is configured to allow the distal end of the catheter and/or a puncturing device deploying from within the catheter, to be desirably oriented within the RAA such that it passes through the cephalad wall of the RAA and into the pericardial space with minimal risk of bystander injury.

The rightward curvature of the transition segment 13 (FIG. 5A) can cause the transition segment to abut the right lateral wall of the RA. The frontward curvature of the transition segment 13 and distal segment 14 (see FIG. 5C) is configured to increase apposition of the distal segment 14 of the catheter to the anterior and/or superior walls of the RA and the RAA, and also serves as a smooth transition from the generally vertical orientation of the proximal segment 12 to the more horizontal orientation of the distal segment 14. In some examples, the distal segment 14 can be oriented in a plane that is generally perpendicular to the proximal segment 12. The distal segment 14 can have a sharper curvature (i.e., smaller radius of curvature) at the anterior aspect of the catheter where the catheter abuts the anterior and/or superior walls of the RA and RAA, relative to the more gently curving transition segment 13 that passes through the caval-atrial junction and the generally straight distal portion 16 that extends into the RAA. The apposition of the distal segment 14 to the anterior and/or superior walls of the RA and RAA cause the distal end 18 to align along the crest of the RAA parallel with the tangential plane of the visceral pericardium and abut the cephalad wall of the RAA, where the distal end 18 is positioned far from the right coronary artery and its branches.

In some examples, the distal segment 14 of the curved catheter can have a radius of curvature of between about 2 inches and about 4 inches, between about 2.5 inches and about 3 inches, and/or about 2.8 inches. In some examples, the distal segment 14 of the curved catheter can have an arc length of between about 90° and about 180°, between about 120° and about 150°, and/or about 135°.

Figure 6:
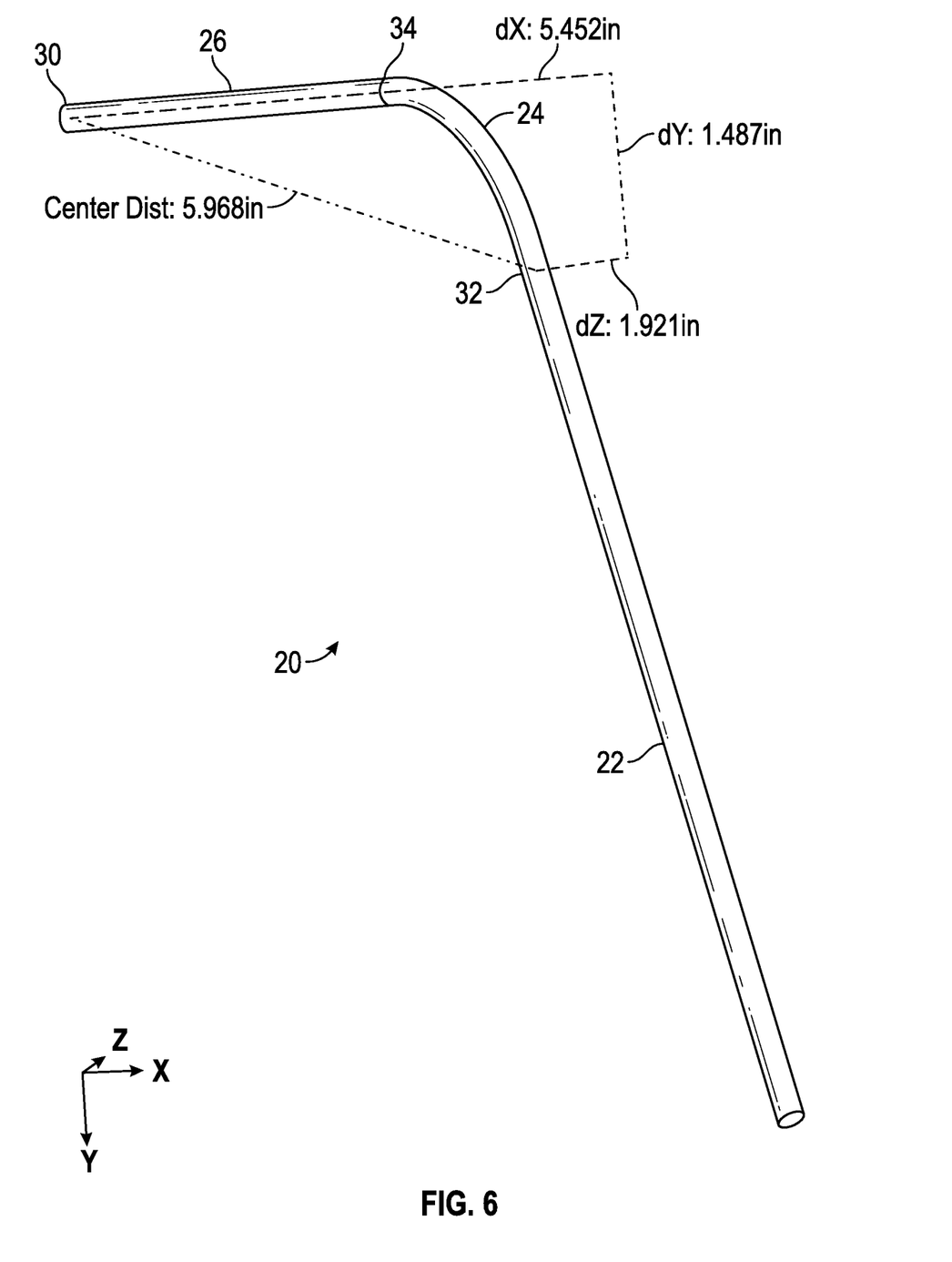
FIGS. 6 and 7 illustrate another exemplary curved catheter.
Figure 7:
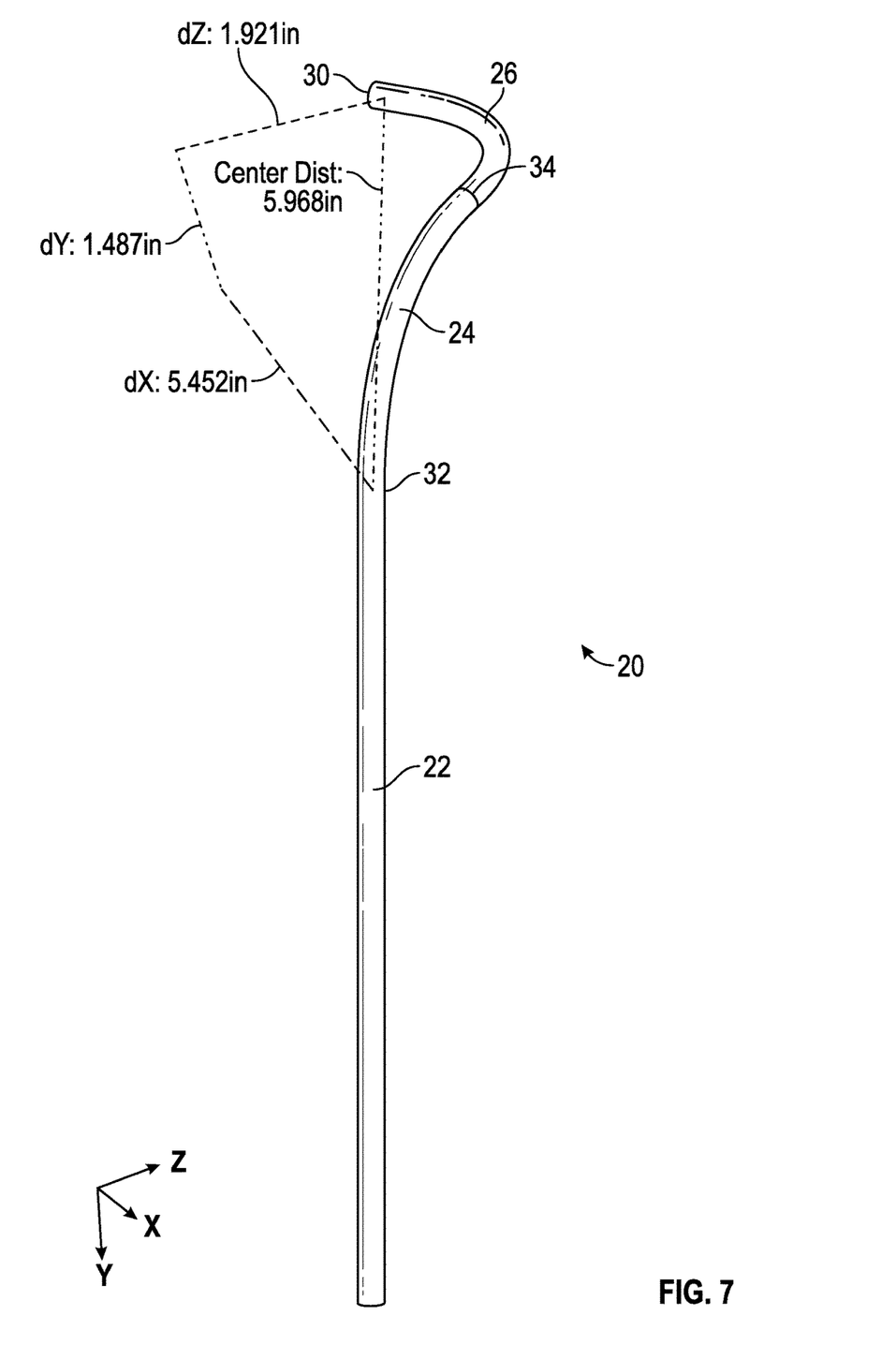

FIGS. 6 and 7 show another exemplary curved catheter 20 that is similar to the catheter 10. FIG. 6 shows a rear view (similar to FIG. 5E) and FIG. 7 shows a right side view (similar to FIG. 5G). The catheter 20 includes a proximal segment 22, a transition segment 24, and a distal segment 26 that terminates in distal end 30. The proximal segment 22 and transition segment 24 are joined at point 32, and the transition segment 24 and distal segment 26 are joined at point 34. FIGS. 6 and 7 include exemplary dimensions for the transition segment 24 and the distal segment 26. For example, the direct distance from the point 32 to the distal end 30 can be about 6 inches.

Figure 8A:
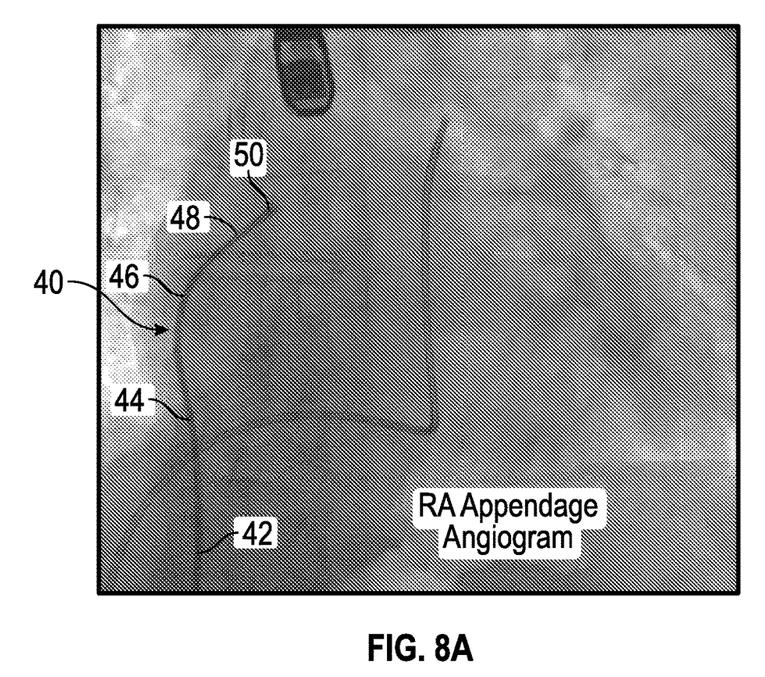
Figure 8B:
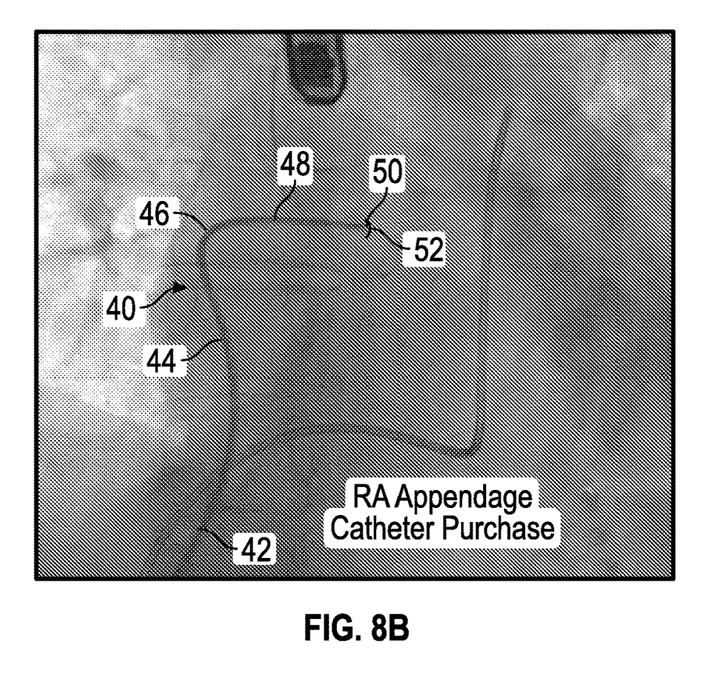
Figure 8C:
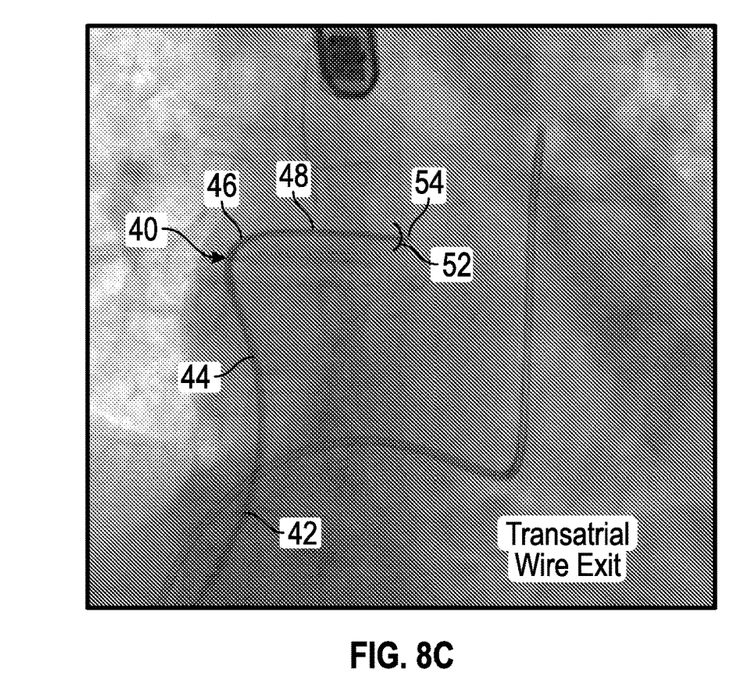
Figure 8D:
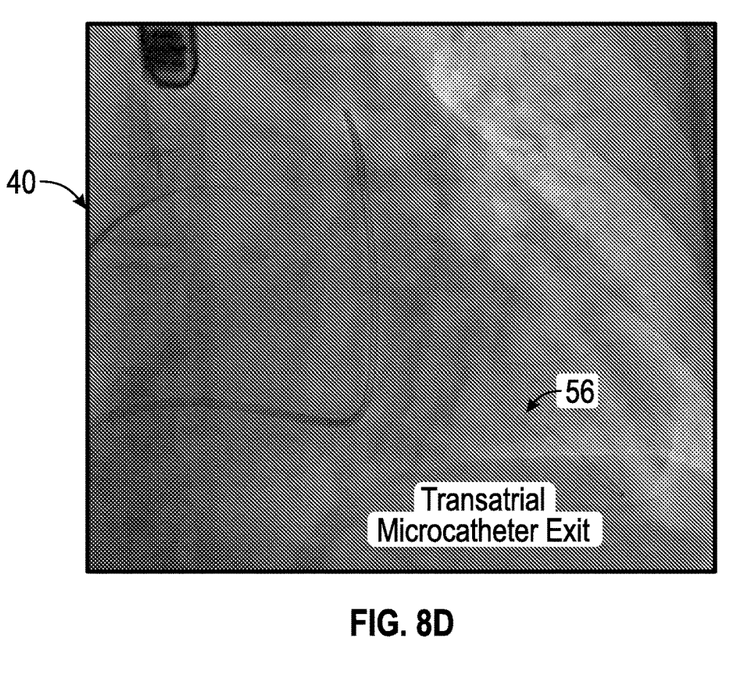

FIGS. 8A-8D are radiographic images showing four stages in an exemplary procedure wherein the pericardial space is accessed via the RAA. In FIG. 8A, an exemplary curved catheter 40 is positioned extending through the IVC with its distal end 50 within the RA. In FIG. 8B, the distal end 50 has advanced into the RAA and abuts a cephalad wall or crest 52 of the RAA. In this position, a proximal segment 42 is within the IVC, a transition segment 44 passes through the caval-atrial junction into the RA, a distal segment 46 abuts the anterior and/or superior walls of the RA and RAA as it curves leftward into the RAA with a straight distal portion 48 projecting through the RAA. In FIG. 8C, a puncturing device 54 is deployed from the distal end of the catheter 50 and punctures through the wall 52 of the RAA in generally horizontal plane and passes into the pericardial space. The puncture device 54 can extend coaxially from within the catheter 40, for example. In some examples, the puncture device can comprise a 0.014 inch wire. FIG. 8D shows an exemplary therapeutic device 56 extending from the catheter 40, through the puncture in the RAA, and into the pericardial space. The device 56 can include a microcatheter that extends over the puncture device/guidewire 54. The device 56 can comprise any of a variety of device for performing a procedure within the pericardial space.

Figure 9A:
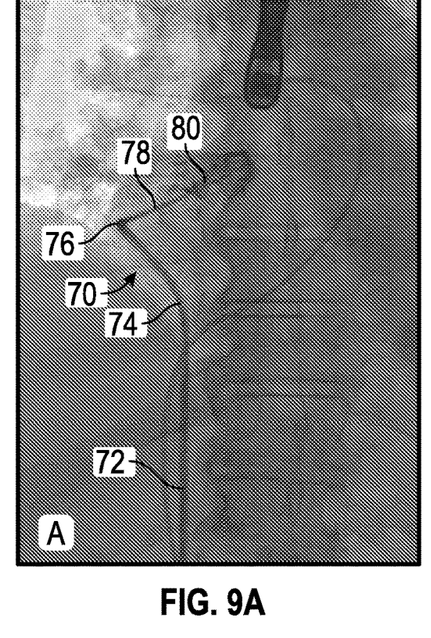
FIGS. 9A-9D are radiographic images illustrating another exemplary procedure using a curved catheter to access the pericardial space through the right atrial appendage.
Figure 9B:
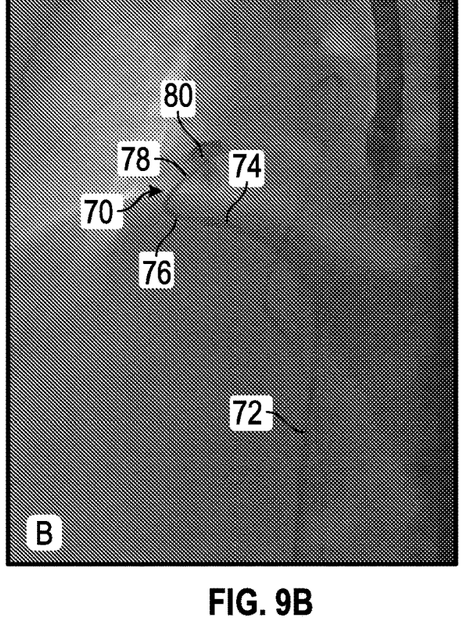
Figure 9C:
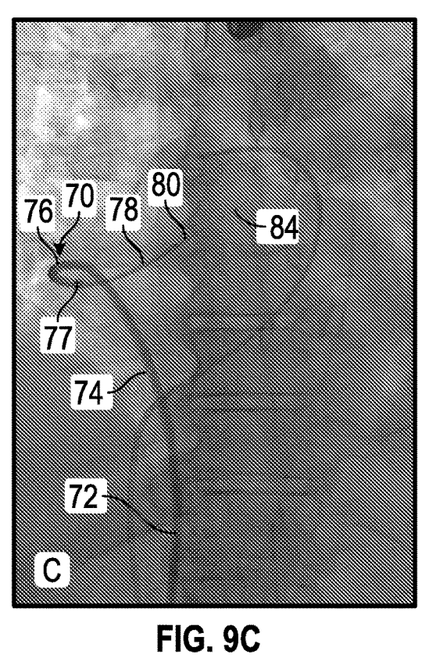
Figure 9D:
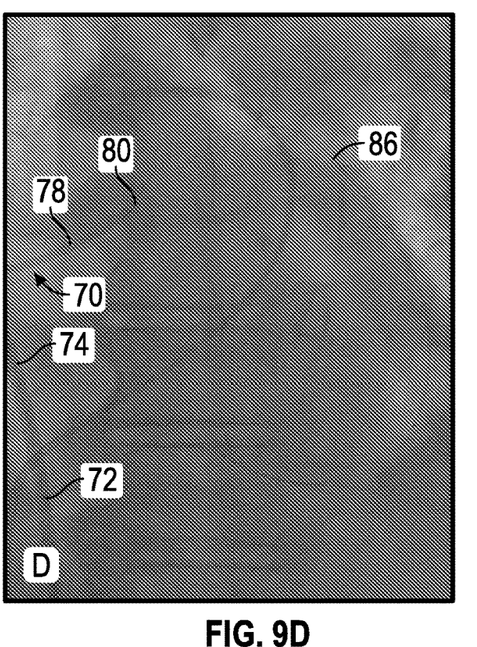

FIGS. 9A-9D are radiographic images showing four stages in another exemplary procedure wherein the pericardial space is accessed via the RAA. In FIG. 9A, an exemplary curved catheter 70 is positioned extending through the IVC with its distal end 80 within the RA. In FIG. 9B, the distal end 80 has advanced into the RAA and abuts a cephalad wall or crest of the RAA. In this position, a proximal segment 72 is within the IVC, a transition segment 74 passes through the caval-atrial junction into the RA, a distal segment 76 abuts the anterior and/or superior wall of the RA and RAA as it curves leftward into the RAA with a straight distal portion 78 projecting through the RAA. In FIG. 9C, a puncturing device 84 is deployed from the distal end of the catheter 70 and punctures through the wall of the RAA in generally horizontal plane and passes into the pericardial space. The puncturing device 84 can include a guidewire. FIG. 9D shows an exemplary therapeutic device 86 extending from the catheter 50, through the puncture in the RAA, and into the pericardial space. The device 86 can include a microcatheter that extends over the puncture device/guidewire 84. The device 86 can comprise any of a variety of devices for performing a procedure within the pericardial space.

Figure 10:
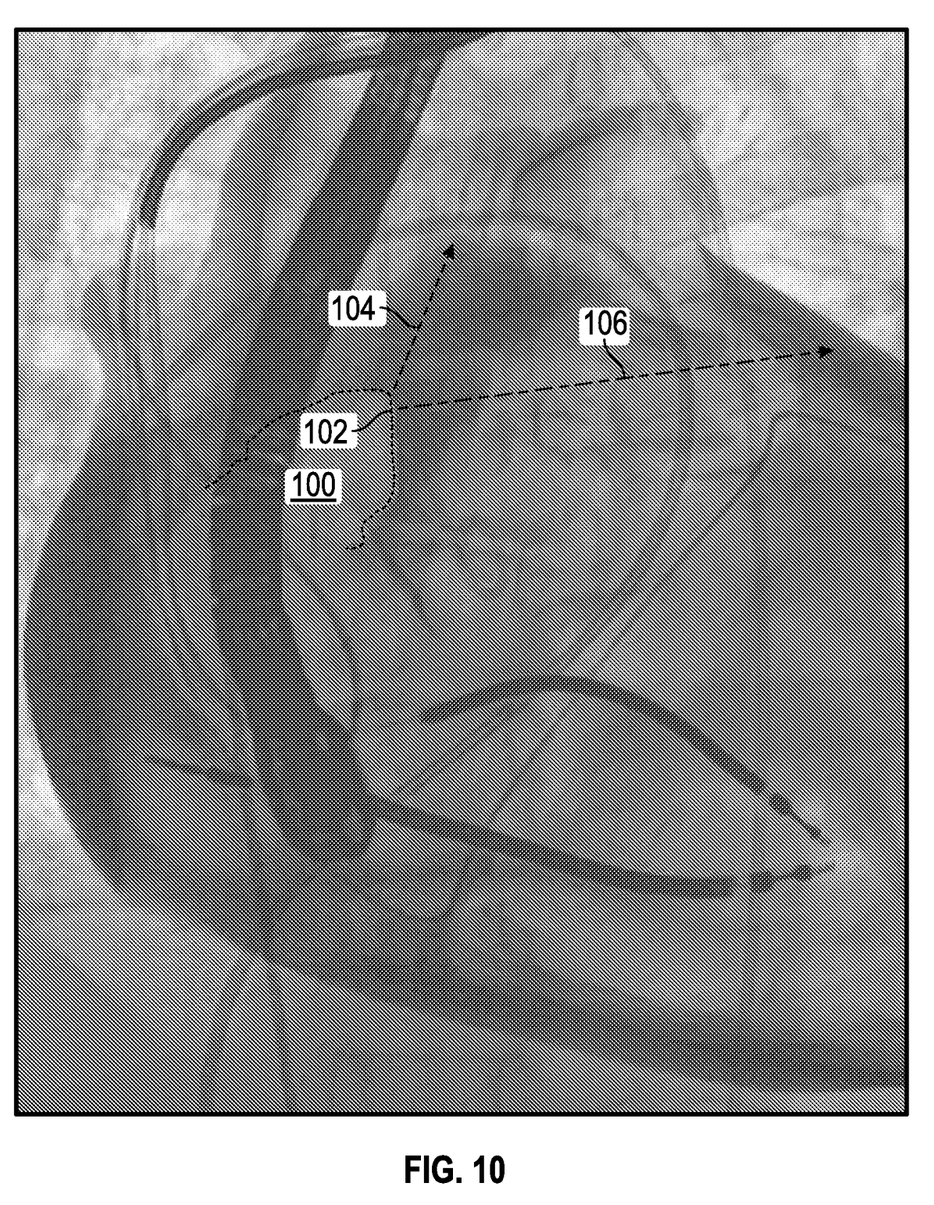
FIG. 10 is a contrast pericardiogram illustrating two alternative exit trajectories from the right atrial appendage.

FIG. 10 illustrates how the disclosed curved catheters can provide a more desirable crossing trajectory when puncturing through the cephalad wall 102 of the RAA 100. With a conventional catheter projecting relatively straight through RA and the RAA, the crossing trajectory is more vertically oriented, as shown by arrow 104. The orientation of the RAA illustrated further in FIGS. 1 and 2, which show the RAA projecting from the RA with a significant vertical tilt. Without the disclosed curved catheter, the crossing trajectory 104 can have an analogous vertical tilt. The trajectory 104 is undesirable as it is transverse to the plane of the pericardium, such that the RAA puncturing device can easily extend too far and also puncture the pericardium. By contrast, the disclosed curved catheters abut the anterior and/or superior walls of the RA and RAA can such that the distal end gives the puncturing device the trajectory 106 that is more horizontal and parallel with the plane of the pericardium, reducing the risk of puncturing the pericardium. The trajectory 106 also helps to avoid other adjacent bystander structures, such as the right coronary artery, pulmonary artery, and aorta. The trajectory 106 also helps direct a therapeutic device more smoothly into the pericardial space without having to make a sharp turn after crossing the wall of the RAA, as is the case with trajectory 104.

A conventional trajectory 104 can be about 36° to about 72° from horizontal, while the disclosed trajectory 106 can be less that 36° from horizontal, less that 30° from horizontal, and/or less than 25° from horizontal. As used here, "horizontal" means in a transverse plane defined by the front, rear, left, and right directions of a patient.

Any of the catheter embodiments disclosed herein can further include, can be used with, or can coaxially deliver, an inflatable balloon catheter that can be inflated at or near the distal end of the catheter to separate and/or flatten the trabeculated walls of the RAA (see FIGS. 1 and 2) to allow distal apposition of the puncturing device against the crest and cephalad wall of the RAA. This can help avoid obstruction by the trabeculations inside the RAA while advancing the catheter along the crest of the RAA to the cephalad wall. Such a balloon catheter can be inflated and deflated any number of times while the curved catheter is advanced through the RAA.

In any of the disclosed embodiments, the curved catheter can be constructed to provide sufficient column strength so that the catheter can provide counter-resistance against the puncturing force applied to the puncturing device while puncturing the RAA wall.

For any of the catheters, systems, and methods disclosed herein, analogous embodiments can be configured for use in a delivery from the superior vena cava (SVC). In such devices the catheter can curve slightly rightward, forward, and downward at the juncture of the SVC and the RA so that it abuts the right lateral wall of the RA, then curve back upward, forward and leftward toward and against the anterior and superior walls of the RA/RAA, then curve slightly rearward, leftward and upward through the RAA.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, groups, dimensions, materials, compounds, or other characteristics described in conjunction with a particular aspect, embodiment or example of the disclosed invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically, magnetically, chemically, electrically, or otherwise coupled or linked and does not exclude the presence of intermediate elements between the coupled elements absent specific contrary language.

In view of the many possible embodiments to which the principles disclosed herein may be applied, it should be recognized that illustrated embodiments are only examples and should not be considered a limitation on the scope of the disclosure. Rather, the scope of this disclosure is at least as broad as the following claims and their equivalents.

The invention claimed is:

1. A transvascular catheter for accessing a pericardial space from within a right atrial appendage (RAA) of a heart, the catheter comprising:
   a proximal segment, a transition segment extending distally from the proximal segment, a distal segment extending distally from the transition segment, and a distal end;
   wherein the catheter extends around and along a central axis that extends substantially parallel with the proximal segment, and wherein the proximal segment is laterally and longitudinally offset from the distal segment relative to the central axis when free of external forces;
   wherein the transition segment and the distal segment extend from the proximal segment with a clockwise three-dimensional spiral curvature around the central axis at least when the catheter is free of external forces, and wherein the clockwise three-dimensional spiral curvature comprises a right-handed chirality such that the catheter curves in a generally clockwise path when viewing the catheter from the proximal segment looking distally along the central axis;
   wherein when the catheter is positioned within a right heart of a patient, the intrinsic spiral curvature of the catheter is such that:
      the proximal segment is positioned within the inferior vena cava;
      the transition segment extends across the caval-atrial junction and curves rightward, forward, and upward such that the catheter abuts a right lateral wall of the right atrium; and
      the distal segment curves leftward, forward, and upward from the transition segment through the right atrium such that the catheter abuts an anterior wall of the right atrium adjacent to the RAA, and the distal segment continues to curve leftward, rearward, and upward from the anterior wall of the right atrium along an anterior-superior wall of the RAA such that the distal end of the catheter contacts a sulcus of the RAA;
   wherein the catheter is configured to guide a coaxial puncturing device to extend from the distal end of the catheter and puncture through the sulcus of the RAA into the pericardial space; and
   wherein the three-dimensional spiral curvature of the catheter orients the distal end of the catheter pointing generally leftward and parallel with the pericardium such that the puncturing device is operable to pass through the sulcus of the RAA and into the pericardial space without damaging the pericardium and at a location spaced apart from the right coronary artery, the pulmonary artery, and the aorta.

2. The catheter of claim 1, wherein the three-dimensional spiral curvature of the catheter orients the distal end of the catheter with a trajectory that is less than 36° from horizontal.

3. The catheter of claim 1, wherein the three-dimensional spiral curvature of the catheter orients the distal end of the catheter with a trajectory that is less than 25° from horizontal.

4. The catheter of claim 1, wherein the distal segment of the catheter has a radius of curvature of between about 2.5 inches and about 3 inches and an arc length of between about 120° about 150°.

5. The catheter of claim 1, further comprising an inflatable balloon that is configured to be inflated within the RAA to separate or flatten trabeculations within the RAA to facilitate advancing the distal end of the catheter against the sulcus of the RAA.

6. The catheter of claim 1, wherein the catheter is configured to deliver a therapeutic device through the puncture in the sulcus of the RAA and into the pericardial space without damaging the pericardium and at a location spaced apart from the right coronary artery, the pulmonary artery, and the aorta.

7. The catheter of claim 1, wherein the distal segment includes a straight portion at the distal end of the catheter.

8. The transvascular catheter of claim 1, wherein a union of the proximal segment and the transition segment comprises a point that is laterally offset by at least 5.50 inches from a point on the distal segment.

* * * * *